United States Patent [19]

Akieda et al.

[11] Patent Number: 5,221,769
[45] Date of Patent: Jun. 22, 1993

[54] PRODUCTION OF P-ACETYLAMINOPHENOL FROM P-AMINOPHENYL ACETATE

[75] Inventors: Hideyuki Akieda; Naoki Sato; Ryuichi Mita; Mitsumasa Umemoto, all of Omuta, Japan

[73] Assignee: Mitsui Toatsu Chemicals Inc., Tokyo, Japan

[21] Appl. No.: 634,999

[22] Filed: Dec. 27, 1990

[30] Foreign Application Priority Data

Dec. 27, 1989 [JP] Japan .................................. 1-336603
Dec. 27, 1989 [JP] Japan .................................. 1-336604

[51] Int. Cl.⁵ .......................................... C07C 233/05
[52] U.S. Cl. .................................... 564/223; 564/216; 564/217
[58] Field of Search ............... 564/217, 139, 144, 216, 564/223

[56] References Cited

U.S. PATENT DOCUMENTS 2,368,073  1/1945  Tyron .................................. 260/561
3,113,150 12/1963  Young ................................. 564/216

OTHER PUBLICATIONS

Feldstein et al., "Acetyl Transfer during Hydrogenation of p-Nitrophenyl Acetate", J. of Org. Chem., vol. 26, No. 5, 1961, p. 1656–1657.
Freifelder, J. Org. Chem., vol. 27, 1962, pp. 1092–1093.
Takeuchi et al., "Photolysis and Thermolysis of Phenyl Azide in Acetic Acid. Trapping of 1-Azacyclohepta-1,2,4,6-tetraene and Nucleophilic Aromatic Substitution", J. Chem. Soc. Perkin Trans. 1, pp. 1269–1273 (1983).

Primary Examiner—Richard L. Raymond
Assistant Examiner—Shailendra Kumar
Attorney, Agent, or Firm—Millen, White & Zelano

[57] ABSTRACT p-Aminophenyl acetate is isomerized to p-acetylaminophenol in the presence of an acid such as acetic acid or phosphoric acid.

8 Claims, 4 Drawing Sheets

PRODUCTION OF P-ACETYLAMINOPHENOL FROM P-AMINOPHENYL ACETATE

BACKGROUND OF THE INVENTION

1. Field of the Invention

The present invention relates to a process for producing p-acetylaminophenol, and more particularly, to a process for producing p-acetylaminophenol by isomerizing p-aminophenyl acetate.

2. Description of the Related Art

There are known various processes for producing p-acetylaminophenol.

Representative processes are:

(1) A process of reacting p-aminophenol with acetic anhydride (for example, U.S. Pat. No. 3113,150, etc.);

(2) A process of dehydration-condensation of p-aminophenol and acetic acid;

(3) A process for reducing p-nitrophenol in the presence of acetic anhydride simultaneously with acetylation [Morris Freifelder: J.Org. Chem., Vol. 27, p. 1092 (1962), U.S. Pat. No. 3,076,030, etc.]; and (4) A process for producing p-acetylaminophenol by rearrangement (Beckmann rearrangement) of an oxime compound in the presence of an acid catalyst, the oxime compound being prepared from p-hydroxyacetonone and hydroxylamine (Eur. Pat. Appl. EP 168,908, etc.).

Among the above-mentioned processes, process (1) is one of the processes widely used in the industrial production. There also are various processes other than above.

A process starting from p-aminophenyl acetate would appear to be suitable as an industrial production process from the standpoints of the starting material and the process step. However, little was known about processes for isomerizing p-aminophenyl acetate to form p-acetylaminophenol. Only one report is described in J. Org. Chem., 26, 1656 (1961) which discloses that it was contemplated to obtain p-aminophenyl acetate by the catalytic reduction of p-nitrophenyl acetate in the presence of platinum oxide as a catalyst in absolute ethanol at a pressure of 60 kg/cm² of hydrogen at 120° C. However, p-aminophenyl acetate was not obtained and instead p-acetylaminophenol was produced in a 77% yield. This fact suggests that p-aminophenyl acetate was in situ isomerized to p-acetylaminophenol.

However, according to our investigation as shown below, it has been found that the isomerization is not effective. That is, when p-aminophenyl acetate prepared separately was isomerized simply by heating p-aminophenyl acetate in an organic solvent, p-acetylaminophenol was formed but at a remarkably slow speed and not in high yield.

For example, FIG. 1 shows a speed of production of p-acetylaminophenol when 0.05 mol. of p-aminophenyl acetate was heated in 15 g. of ethyl cellosolv at 120° C. As is clear from this result, even after 6 hours of the reaction, the production percentage of p-acetylaminophenol is as low as about 40%.

The production percentage, i.e. "production (%)", in the ordinate of FIG. 1–FIG. 4 indicates how much percent of the starting material, p-aminophenyl acetate, is isomerized to p-acetylaminophenol.

Further, in other solvents the results were also almost the same as above, which indicates that the formation of p-acetylaminophenol by catalytic reduction of p-nitrophenyl acetate disclosed in the above-mentioned literature reference involves some other mechanism as well as the isomerization of p-aminophenyl acetate.

SUMMARY OF THE INVENTION

It is an object of the present invention to provide a process for producing p-acetylaminophenol from p-aminophenyl acetate which can easily be practiced industrially.

It is another object of the present invention to provide a process for producing p-acetylaminophenol from p-aminophenyl acetate under mild conditions and in high yield.

It is a further object of the present invention to provide a new and valuable industrial process for producing p-acetylaminophenol.

According to the present invention, there is provided a process for producing p-acetylaminophenol which comprises isomerizing p-aminophenyl acetate in the presence of an acid.

DESCRIPTION OF THE PREFERRED EMBODIMENTS

Figure 1:
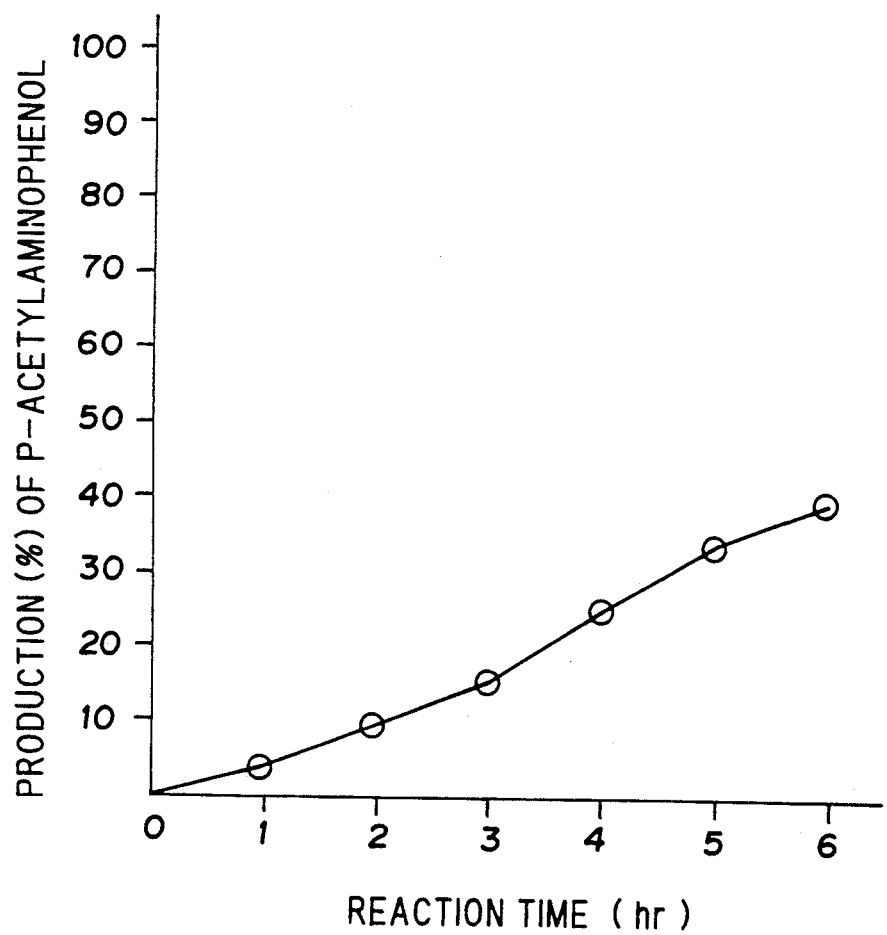
FIG. 1 is a graph showing the rate of production of p-acetylaminophenol by the isomerization of p-aminophenyl acetate in ethyl cellosolv.
Figure 2:
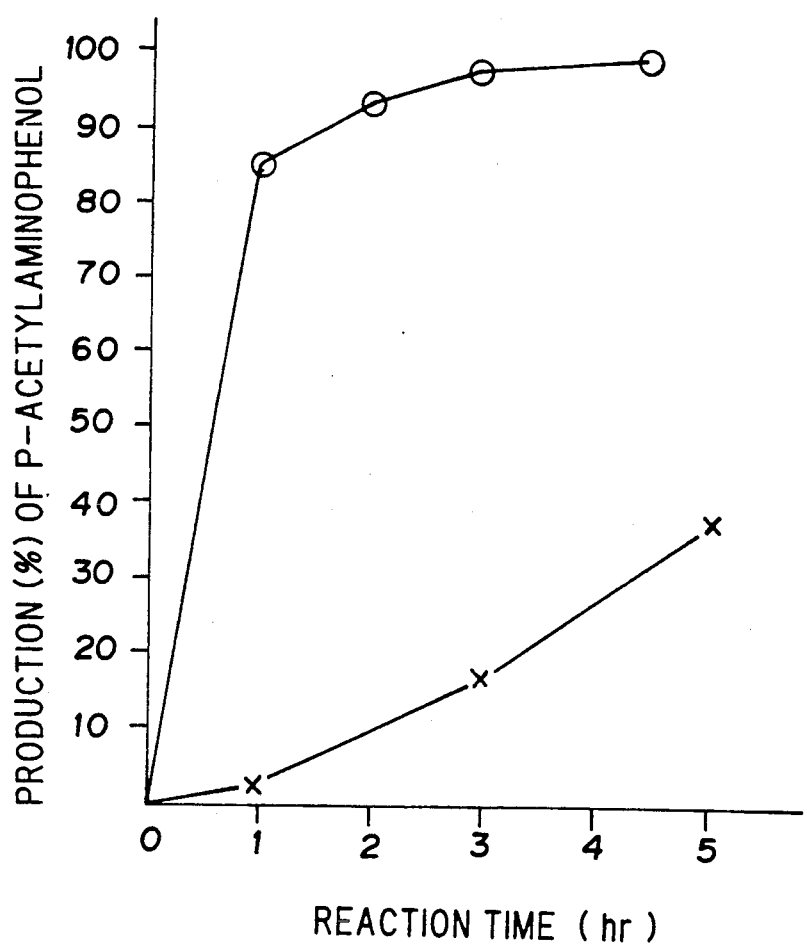
FIG. 2 is a graph showing the rate of production of p-acetylaminophenol by the isomerization of p-aminophenyl acetate in sec-butanol either in the presence of (—⊖—⊖—) or absence of (—x—x—) acetic acid.

FIG. 2 shows the relationship between reaction time and rate of production of p-acetylaminophenol in terms of production percentage when 0.05 mol. of p-aminophenyl acetate was subjected to isomerization at 100° C. in sec-butanol (15 g.) either in the presence of acetic acid (0.005 mol.) or in the absence of acetic acid.

Figure 3:
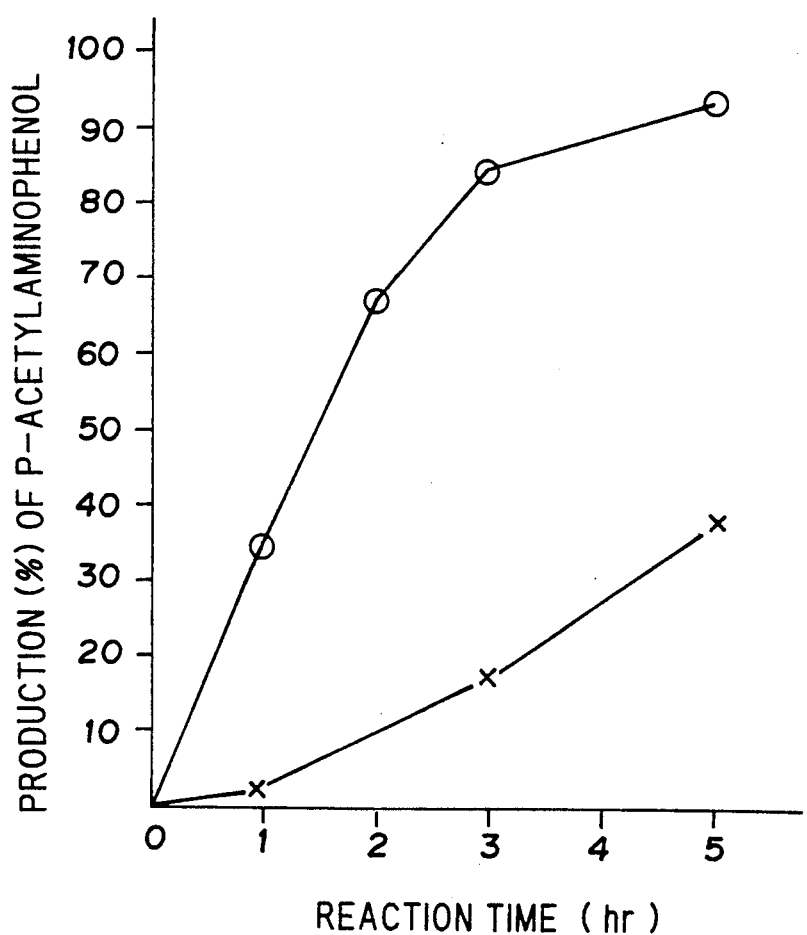
FIG. 3 is a graph showing the rate of production of p-acetylaminophenol by the isomerization of p-aminophenyl acetate either in the presence of (—⊖—⊖—) or absence of (—x—x—) phosphoric acid.

FIG. 3 shows the relationship between reaction time and rate of production of p-acetylaminophenol in terms of production percentage when 0.1 mol. of p-aminophenyl acetate was subjected to isomerization at 100° C. in sec-butanol (15g.) in the presence of phosphoric acid (0.01 mol.) or in the absence of phosphoric acid.

As is clear from these graphs, it has been found that the production percentages of p-acetylaminophenol even after 5 hours of the reactions are less than 40% in the absence of an acid. In contradistinction, when 10 mol. % of acetic acid is present based on the starting p-aminophenyl acetate, the production percentage of p-acetylaminophenol exceeds 95% in 3 hours and when 10 mol. % of phosphoric acid is present based on the starting p-aminophenyl acetate, the production percentage of p-acetylaminophenol exceeds 90% in 5 hours.

Figure 4:
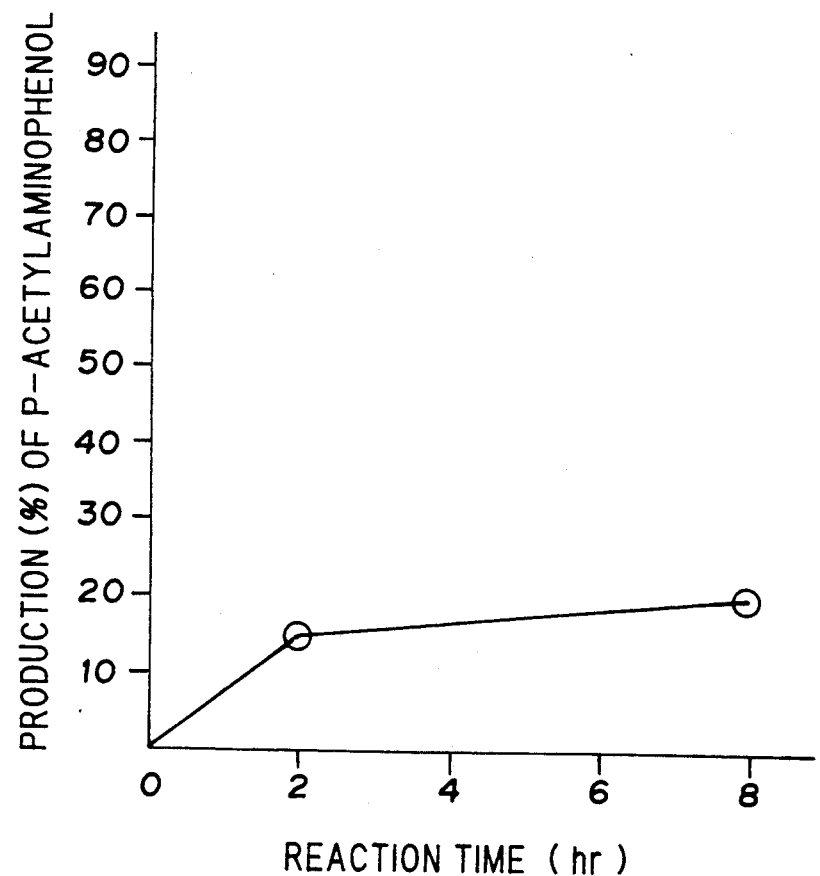
FIG. 4 is a graph showing the rate of production of p-acetylaminophenol by the reaction of p-aminophenol with acetic acid.

The rate of production of p-acetylaminophenol at 102°–103° C. in a system employing p-aminophenol (0.1 mol.) and acetic acid (0.11 mol.) in sec-butanol (30 mol.) was also investigated and found to be remarkably slow, as shown in FIG. 4.

The present invention has been completed by developing further the above-mentioned knowledge.

That is, according to the present invention, p-acetylaminophenol is produced by isomerizing p-aminophenyl acetate in the presence of an acid, preferably by heating a reaction mixture consisting essentially of p-aminophenyl acetate, a reaction solvent and an amount of an acid effective to isomerize the p-aminophenyl acetate to p-acetylaminophenol.

p-Aminophenyl acetate, the starting material of the present invention, may be produced in high yield by reacting p-aminophenol with benzaldehyde to form a Schiff base, reacting the Schiff base with acetic anhydride to form an acetoxy compound and treating the compound with a mineral acid, such as hydrochloric acid, sulfuric acid and the like.

A more efficient process for producing p-aminophenyl acetate previously proposed by the present inventors preferably comprises reacting p-nitrophenol with acetic anhydride or reacting p-nitrohalogenobenzene with sodium acetate or potassium acetate to form p-nitrophenyl acetate and then catalytically reducing the resulting p-nitrophenyl acetate in the presence of a reducing catalyst at a temperature of 50° C. or less.

In one aspect of this invention, the starting p-aminophenyl acetate is used without purification in the form of the solution obtained by the reduction of p-nitrophenyl acetate as described above.

Although the process of the present invention can be effected in the absence of a solvent, it usually is conducted in an inert (with respect to the reaction) organic solvent. The organic solvent is not particularly critical and a wide variety of solvents may be used.

Exemplary suitable organic solvents include: alcoholic solvents such as methanol, ethanol, n-propanol, isopropanol, n-butanol, sec-butanol, isobutanol, tert-butanol, methyl cellosolv, ethyl cellosolv and the like; aliphatic or aromatic hydrocarbon solvents such as petroleum ether, hexane, heptane, octane, benzene, toluene, xylene, ethylbenzene, decaline and the like; aliphatic or aromatic halogenated hydrocarbon solvents such as dichloromethane, chloroform, carbon tetrachloride, dichloroethane, trichloroethane, trichloroethylene, Perclene, chlorobenzene, dichlorobenzene, trichlorobenzene and the like; ether solvents such as diethyl ether, diisopropyl ether, diisobutyl ether, tetrahydrofuran and the like; ketone solvents such as acetone, methyl ethyl ketone, diisobutyl ketone and the like; ester solvents such as methyl acetate, ehtyl acetate, butyl acetate and the like; carboxylic acid solvents such as acetic acid, propionic acid and the like; nitrogen-containing non-basic solvents such as N-methylpyrrolidone, N,N-dimethylformamide, N,N-diethylformamide, N,N-dimethylacetamide, N,N-diethylacetamide, N,N'-dimethylimidazolidinone, N,N'-dimethylpropyleneurea, nitrobenzene and the like; sulfur-containing solvents such as dimethylsulfoxide, sulfolane and the like; glycol solvents such as ethylene glycol, diethylene glycol, triethylene glycol, ethylene glycol dimethyl ether, diethylene glycol dimethyl ether and the like; phosphoric acid ester solvents such as triethyl phosphate, tributyl phosphate and the like.

Naturally, the solvents enumerated here are only some examples and therefore, the solvents used in the present invention are not limited to those solvents. The solvents are usually used alone, but may be used in combination of two or more.

According to the present invention, when a solvent miscible with water is used, the solvent may be used as a mixture with water as far as the essence of the present invention is not impaired.

The amount of the solvent is not particularly limited, but, taking into consideration the volume efficiency of the reaction, the amount is usually up to 20 times the weight of p-aminophenyl acetate as the starting material.

The feature of the process of the present invention is the isomerization reaction of p-aminophenyl acetate in the presence of an acid and as a result, p-aminophenyl acetate can be converted efficiently to p-acetylaminophenol.

As the acid, there may be used both organic acids and inorganic aicds.

Examples of organic acids which may be used are aliphatic and aromatic carboxylic and sulfonic acids. Some of these organic acids are soluble in the reaction system while others, for example, solid acids, are not. However, both may be used in the present invention.

Examples of suitable aliphatic carboxylic acids include substituted and unsubstituted mono and polycarboL xylic acids, e.g., of 1-8 carbon atoms, e.g., formic acid, acetic acid, monochloroacetic acid, dichloroacetic acid, trichloroacetic acid, propionic acid, oxalic acid, maliic acid, funaric acid and the like.

Examples of suitable aromatic carboxylic acids include substituted and unsubstituted mono and polycyclic carboxylic acids, e.g., of 6 to 12 ring carbon atoms, e.g., benzoic acid, phthalic acid, isophthalic acid, terephthalic acid, and ion exchange resins of the weak acid type, and the like.

Examples of suitable aliphatic sulfonic acids include substituted and unsubstituted mono and polysulfonic acids, e.g., of 1-8 carbon atoms, e.g., methane sulfonic acid, ethane sulfonic acid, hexane sulfonic acid, heptane sulfonic acid, perfluoropolyalkane sulfonic acid ("Nafion", tradename, supplied by Du Pont) and the like.

Examples of suitable aromatic sulfonic acids include substituted and unsubstituted mono and polycyclic sulfonic acids, e.g., of 6 to 12 ring carbon atoms, e.g., benzene sulfonic acid, p-toluene sulfonic acid, p-ethylbenzene sulfonic acid, ion exchange resins of a strong acid type and the like.

Among the organic acids, acetic acid is particularly preferable.

As inorganic acids, various acids can be mentioned. One of the groups of inorganic acids is a protonic acid. Exemplary suitable protonic acids include hydrochloric acid, hydrobromic acid, hydroiodic acid, sulfuric acid, phosphoric acid (ortho),polyphosphoric acid, perchloric acid, carbonic acid and the like. Another group of inorganic acids are Lewis acids: Exemplary suitable Lewis acids include aluminum chloride, aluminum bromide, aluminum sulfate, ferric chloride, ferric bromide, ferric sulfate, stannous chloride, stannous bromide, copper acetate, zinc chloride, zinc bromide, zinc sulfate, titanium tetrachloride, titanium tetrabromide, phosphorus pentaoxide, boron trifluoride and the like. The Lewis acids may be in a water-containing form.

A further group of inorganic acid is a heteropolyacid. Examplary suitable heteropolyacids include phosphotungstic acid, silicotungstic acid, phosphomolybdic acid, sodium phosphomolybdate, phosphotungstomolybdic acid, phosphovanadomolybdic acid and the like.

Among the inorganic acids, ortho-phosphoric acid is preferred. When these acids are used in too small an amount, the purpose of the present invention is not fully attained. Conversely, when they are used in too large an amount, by-products, i.e. impurities, are liable to form. Therefore, the acid is usually used in an amount of from 0.1 to 200 mole %, preferably from 1 to 100 mole % and most preferably from 1 to 20 mole %, based on the starting material, p-aminophenyl acetate, except in the case of relatively weak organic acids, such as acetic acid, which can be used as a reaction solvent.

According to the present invention, the order of adding the p-aminophenyl acetate, the solvent and the acid used as a catalyst to the reaction zone is not particularly critical. For example, the p-aminophenyl acetate can be dissolved or suspended in the solvent and a prescribed amount of an acid added thereto, or the p-aminophenyl acetate can be fed to a solvent to which an acid has previously been added. The resulting mixture is then heated to a selected temperature at which the reaction is effected.

Since both the starting material and the resulting p-acetylaminophenol are susceptible to becoming discolored in an oxidizing atmosphere when heated, the reaction is preferably carried out in an inert atmosphere, e.g., nitrogen gas.

When the reaction temperature is too low, the reaction rate is lowered whereas at too high a temperature impurities are liable to be formed as by-products. Therefore, the reaction temperature is usually 30°–200° C., preferably 50°–150° C., more preferably 80°–130° C. Under such temperature conditions, the contemplated reaction is substantially completed usually within about 30 hours or less, usually 8 hours or less, and often within hours.

The p-acetylaminophenol produced by the isomerization of p-aminophenyl acetate may be separated from the reaction system according to the present invention by various conventional separation methods. One example of such a separation is described below.

When the p-acetylaminophenol precipitates as crystals from the reaction system after the reaction is complete and, if necessary, after the reaction mixture is cooled and/or some or most of the solvent is distilled off under reduced pressure, the crystals are then separated by a solid-liquid separation procedure such as vacuum filtration and the like, was washed with water, and further purified, if desired, by a purification procedure such as recrystallization and the like.

If the resulting p-acetylaminophenol does not crystallize from the reaction system after the reaction, even after cooling, the reaction solvent can be distilled off under reduced pressure and the residue washed with water to obtain crude p-acetylaminophenol which can be purified, for example, by recrystallization or the like.

As is clear from the above, the process of the present invention can produce p-acetylaminophenol under mild conditions in good yield from p-aminophenyl acetate which thus can be industrially produced without difficulty. The process is a valuable industrial process taking account of the starting material and the reaction operation.

The present invention will be explained further in detail in the following examples.

Conditions of analysis by high performance liquid chromatography are as shown below.

Column: YMC Pack A-314 (ODS) 6 mm $\phi \times 25$ cm (manufactured by Yamamura Kagaku Kenkyusho)

Mobile phase: 0.05 mol. $KH_2PO_4$ aq./methanol = 6/4 (volumetric ratio) pH = 5.5

10 Flow rate: 0.4 ml./min.

Detector: Ultraviolet spectrophotometer wavelength = 245 nm

EXAMPLE 1

To a 50 ml. four-necked flask equipped with a thermometer, a stirrer, and a condenser were added p-aminophenyl acetate 7.50 g. (0.05 mol.), sec-butanol 15 g and acetic acid 600 mg. (20 mol. % based on p-aminophenyl acetate) and the reaction was carried out in a mild nitrogen stream at 100° C. for 5 hours.

After completion of the reaction, the solvent was distilled off under vacuum to give crude crystal of p-acetylaminophenol (7.89g.).

The result of analysis by high performance liquid chromatography indicated that the content of p-acetylaminophenol was 95%. The weight yield was 99.9% based on the p-aminophenyl acetate. The resulting solid was recrystallized in ethyl acetate to obtain a pure white crystals, melting point 167°–168° C. (literature: 168°–169° C.).

EXAMPLE 2

To a 50 ml. four-necked flask equipped with a thermometer, a stirrer, and a condenser were added p-aminophenyl acetate 7.50 g. (0.05 mol.), xylene 7.50 g. and p-toluenesulfonic acid monohydrate 951 mg. (10 mol. % based on the p-aminophenyl acetate), and the reaction was carried out at 130° C. for 3 hours under a mild nitrogen stream.

After cooling, the precipitated crystals were subjected to a vacuum filtration to separate the crystals and washed with water followed by drying under a reduced pressure, and 7.20 g of a product was obtained.

The analysis of the product by high performance liquid chromatography indicated that the content of p-acetylaminophenol was 94.7%. The yield was 90.9% based on the p-aminophenyl acetate.

EXAMPLES 3–8

The procedure in Example 1 or 2 was repeated except that the reaction solvents (type and amount), the reaction conditions (temperature and time) and the catalyst (type and amount)were varied. The results are shown in Table 1.

Separation of the product was effected by distilling off most of the solvent under reduced pressure after the reaction, washing the residue with water, filtering and drying.

EXAMPLES 9–12

The procedure of Example 1 or 2 was repeated using acetic acid as the catalyst, sec-butanol as the reaction solvent, and 100° C. as the reaction temperature except that the amounts of acetic acid and sec-butanol and the reaction time were varied. The results are shown in Table 2.

EXAMPLE 13

To a 50 ml. four-necked flask equipped with a thermometer, a stirrer and a condenser were added p-aminophenyl acetate 7.50 g. (0.05 mol.), xylene 7.5 g., and aluminum chloride hexahydrate 0.180 g. (1.5 mol. % based on p-aminophenyl acetate) and the reaction was effected by heating under reflux at 130° C. for 2 hours. After cooling, the resulting precipitated crystals were subjected to vacuum filtration and the thus separated crystals were washed with water and dried under reduced pressure.

7.21 g. of crude crystal of p-acetylaminophenol was obtained and analyzed by high performance liquid chromatography. The content of p-acetylaminophenol was 95.3%. The yield was 91.6% based on the p-aminophenyl acetate.

EXAMPLE 14

To a 50 ml. four-necked flask equipped with a thermometer, a stirrer and a condenser were added p-aminophenyl acetate 7.50 g. (0.05 mol.), n-butanol 7.50 g. and titanium tetrachloride 0.14 g. (1.5 mol. % based on p-aminophenyl acetate) and the reaction was carried out in a nitrogen atmosphere at 100° C. for 5 hours.

After completion of the reaction, the reaction fluid was concentrated under reduced pressure to give 7.79 g. of crude crystalline p-acetylaminophenol. The result of analysis by high performance liquid chromatography indicated that the content of p-acetylaminophenol was 90.3%. The yield was 93.8% based on the p-aminophenyl acetate.

EXAMPLES 15–19

The procedure of Example 13 or 14 was repeated except that the reaction solvent (type and amount), reaction conditions (temperature and time) and catalyst (type and amount) were varied. The results are shown in Table 3.

COMPARATIVE EXAMPLE 1

To a 50 ml. four-necked flask were added p-aminophenyl acetate 7.50 g. (0.05 mol.) and ethyl cellosolv 15 g, and heated under reflux for 5 hours at a reaction temperature of 120° C.

After completion of the reaction, the solvent was distilled off under reduced pressure to give 7.78 g. of crude crystalline of p-acetylaminophenol, which was uniformly pulverized and analyzed by high performance liquid chromatography. The content of p-acetylaminophenol was 41.6% and the yield was 43.2% based on the p-aminophenyl acetate.

COMPARATIVE EXAMPLE 2

To a 50 ml. four-necked flask were added p-aminophenol 10.9 g. (0.1 mol.), acetic acid 6.6 g. (0.11 mol.) and sec-butanol 30 ml., and heated under reflux for 8 hours of a reaction temperature of 102°–103° C.

After completion of the reaction, the solvent was distilled off to give 11.8 g. of crude crystalline of p-acetylaminophenol. This solid was uniformly pulverized and analyzed by high performance liquid chromatography. The content of p-acetylaminophenol was 25.7% and the yield was 20.1% based on the p-aminophenol.

TABLE 1

Preparation of p-acetylaminophenol by isomerization of p-aminophenyl acetate in the presence of various inorganic acids

| Note 1) Example | Reaction Solvent Amount (g) | Catalyst Type/Amount (mole %/based on p-aminophenyl acetate) | Reaction Condition Temperature (°C.)/ Time (hrs) | Yield (g) | Purity (%) | Yield (%/based on p-aninophenyl acetate) |
|---|---|---|---|---|---|---|
| 3 | Methyl Cellosolv/15 | Benzoic acid/5 | 120/5 | 7.53 | 73.4 | 73.7 |
| 4 | Chlorobenzene/60 | Nafion-H/100 (mg) | 130/4 | 7.38 | 77.0 | 75.3 |
| 5 | Xylene/45 | Methanesulfonic acid/15 | 130/4 | 7.48 | 80.3 | 80.1 |
| 6 | Butyl acetate/30 | Amberlite IR-120/10 | 125/3 | 7.32 | 85.2 | 83.2 |
| 7 | — | Acetic acid/1 | 80/1 | 7.49 | 80.4 | 80.3 |
| 8 | Acetic acid/15 | — | 110/2 | 7.38 | 96.8 | 95.3 |

Note 1): The reaction scale was the same as that in Example 1 in terms of mole number.

TABLE 2

Effect of amounts of sec-butanol and acetic acid and reaction time

| Note 1) Example | Solvent Amount (g) | Catalyst Amount (mole %/based on p-aminophenyl acetate) | Reaction Condition Temperature (°C.)/ Time (hrs) | Yield (g) | Purity (%) | Yield (%/based on p-aminophenyl acetate) |
|---|---|---|---|---|---|---|
| 9 | 7.5 | 1 | 100/6 | 7.63 | 97.2 | 98.9 |
| 10 | 15.0 | 5 | 100/5 | 7.54 | 94.5 | 95.0 |
| 11 | 15.0 | 10 | 100/5 | 7.52 | 97.0 | 97.3 (FIG. 2) |
| 12 | 30.0 | 20 | 100/5 | 7.58 | 93.0 | 94.1 |

Note 1): The reaction scale was the same as that in Example 1 in terms of mole number.

TABLE 3

Preparation of p-acetaylaminophenol by isomerization of p-aminophenyl acetate in the presence of various inorganic acids

| Note 1) Example | Reaction solvent Amount (g) | Catalyst Type/Amount (mole %/based on p-aminophenyl acetate) | Reaction Condition Temperature (°C.)/ Time (hrs) | Yield (g) | Purity (%) | Yield (%/based on p-aminophenyl acetate) |
|---|---|---|---|---|---|---|
| 15 | Methyl Cellosolv/7.5 | Stannous chloride/5 | 120/5 | 7.48 | 82.5 | 82.3 |
| 16 | Chlorobenzene/60 | Phosphomolybdic acid/20 (mg) | 130/4 | 7.31 | 72.0 | 70.1 |
| 17 | Butyl acetate/15 | Conc. hydrochloric acid/5 | 125/4 | 7.33 | 91.3 | 89.2 |
| 18 | sec-Butanol/15 | Phosphoric acid/5 | 100/6 | 7.54 | 94.3 | 94.8 |
| 19 | — | Cupric oxide/5 | 80/1 | 7.51 | 93.1 | 93.2 |

Note 1): The reaction scale was the same as Example 13 in terms of mole number.

COMPARATIVE EXAMPLE 3

7.50 g (0.05 mol.) of p-aminophenyl acetate was fed to a 50 ml. four-necked flask, melted at a reaction temperature of 80° C. and kept at that temperature for 5 hours, and 7.45 g. of crude crystals were obtained which were uniformly pulverized and analyzed by high performance liquid chromatography. The content of p-acetylaminophenol was 40.6% and the yield was 40.3% based on p-aminophenyl acetate.

What is claimed is:

1. A process for producing p-acetylaminophenol which comprises isomerizing p-aminophenyl acetate in the presence of an inorganic acid selected from the group consisting of protonic acids, Lewis acids and heteropoly acids or an organic acid selected from the group consisting of carboxylic acids and sulfonic acids.

2. A process according to claim 1 in which the inorganic acid is phosphoric acid.

3. A process according to claim 1 in which the acid is an aliphatic carboxylic acid.

4. A process according to claim 3 in which the aliphatic carboxylic acid is acetic acid.

5. A process according to claim 1 in which from 1 to 20 mole % of acid, calculated on the starting p-aminophenyl acetate, is employed.

6. A process according to claim 1 in which the reaction is conducted at 80° to 130° C.

7. A process according to claim 1 in which the reaction is conducted in an inert atmosphere.

8. A process according to claim 5 in which the acid is acetic acid or orthophosphoric acid and the reaction is conducted in a reaction solvent at 80° to 130° C. in an inert atmosphere.

* * * * *